Figure 1:
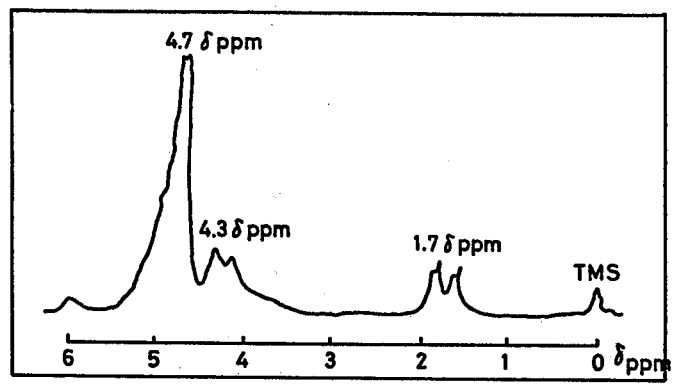

United States Patent [19]
Umetani et al.

[11] 4,166,897
[45] Sep. 4, 1979

[54] PHOSPHORUS-CONTAINING CONDENSATION PRODUCTS, THEIR PRODUCTION AND THEIR USE AS FLAME RETARDANTS

[75] Inventors: Kohei Umetani; Masakazu Date, both of Takatsuki; Kiyonori Kawai, Toyama, all of Japan

[73] Assignee: Toyo Boseki Kabushiki Kaisha, Osaka, Japan

[21] Appl. No.: 710,856

[22] Filed: Aug. 2, 1976

[30] Foreign Application Priority Data

Aug. 5, 1975 [JP] Japan .................................. 50-95573

[51] Int. Cl.$^2$ ............................................... C08G 79/06
[52] U.S. Cl. ............................ 528/398; 260/606.5 P; 427/390 D; 428/365
[58] Field of Search .................. 260/2 P, 606.5 P; 528/398

[56] References Cited

U.S. PATENT DOCUMENTS

| 2,809,941 | 10/1957 | Reeves et al. | 260/2 P |
| 3,146,212 | 8/1964 | Wagner et al. | 260/2 P |
| 3,932,502 | 1/1976 | Nachbur et al. | 260/2 P |
| 4,071,501 | 1/1978 | Pepperman et al. | 260/2 P |

FOREIGN PATENT DOCUMENTS 951988  3/1964  United Kingdom ..................... 260/2 P Primary Examiner—Wilbert J. Briggs, Sr.
Attorney, Agent, or Firm—Wenderoth, Lind & Ponack

[57] ABSTRACT

Process for producing a water-soluble phosphorus-containing condensation product having a molar ratio P—CH$_2$—P linkage/P—CH$_2$OCH$_2$—P linkage of 0.8–4.0 by heating a tetrakis(hydroxymethyl)phosphonium compound under reduced pressure and acid conditions to condense it by dehydration and deformaldehydation reaction. This condensation product can be used for rendering textile articles flame retardant.

13 Claims, 2 Drawing Figures

PHOSPHORUS-CONTAINING CONDENSATION PRODUCTS, THEIR PRODUCTION AND THEIR USE AS FLAME RETARDANTS

The present invention relates to an improved process for the manufacture of water-soluble phosphorous-containing condensation products for treating textile articles, particularly for blended textile articles of meltable synthetic fibers and non-meltable natural fibers, to which it is difficult to impart durable flame retardancy. The invention also relates to said products and to a process for treating textile articles by using said products.

It is known to use water-soluble condensation products of a tetrakis(hydroxymethyl)phosphonium compound (hereinafter abbreviated as THP compound) as durable flame retardants for treating textile articles. For example, U.S. Pat. No. 3,221,057 (British Pat. No. 951,988) describes a process for the synthesis of water-soluble condensation products, wherein a THP compound is condensed at 150°–200° C., under bubbling of an inert gas through the reaction liquid, and a process for the flame retardant treatment of textile articles with said products. However, in the case of the condensation products obtained by the reaction under bubbling of an inert gas through the reaction liquid, the condensation occurs after the THP compound has been decomposed into a phosphine, as shown by the following reaction formula described in its specification:

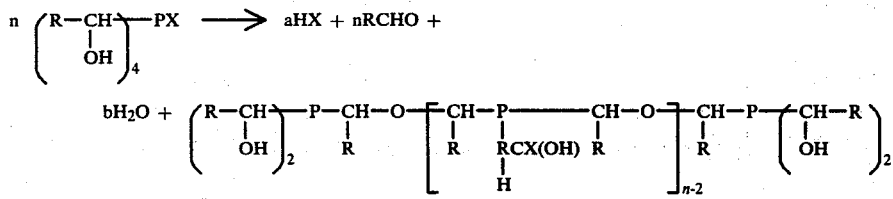

or the condensation product is decomposed into a phosphine. Such phosphine type condensation products have a high content of phosphorus, but the proportion of the content of the following phosphonium group having a high reaction activity is small, and thus the reactivity is markedly lowered.

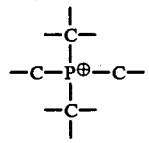

In addition, since they decompose into a phosphine, the condensation reaction proceeds with difficulty, and moreover they have a very disagreeable odor due to the coexisting low molecular phosphines. Therefore, when applied to textile articles, they require a large amount of fixing agents, giving a stiff hand and low strength. Furthermore, they worsen the working environment by emitting the disagreeable odor.

Further, Laid-open Japanese Patent Application (KOKAI) No. 47-3345 describes a process for the synthesis of a water-soluble condensation product obtained by condensing a THP compound in a non-aqueous solution, particularly in the presence of an inert organic solvent at 100°–150° C., and a process for the flame retardant treatment of textile articles with said condensation product. However, when a THP compound is condensed singly at these temperatures, especially at about 135° C., a condensation product composed mainly of methylene ether linkages is formed by dehydration reaction, as shown by the following formula described in its specification:

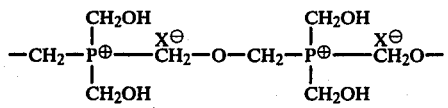

even when the condensation is carried out under reduced pressure. This condensation product has a large proportion of phosphonium groups and the reaction activity of the remaining hydroxymethyl groups is higher than that of the condensation product obtained in U.S. Pat. No. 3,221,057, so that the product can be fixed firmly enough with a small amount of a fixing agent. But for obtaining sufficiently durable flame retardancy, a large amount of a fixing agent is required as in U.S. Pat. No. 3,221,057, because the methylene ether linkages in said condensation product are poor in stability against hydrolysis. Furthermore, when the THP compound is condensed especially in an inert solvent, a characteristic disagreeable odor is given off as described in its specification because the by-produced phosphine does not condense sufficiently.

Also, water-soluble condensation products obtained by heat-condensing a THP compound with an amino-group-containing compound such as urea or dicyandiamide, under ordinary pressure, are known from U.S. Pat. Nos. 3,878,245 and 3,931,310. These patents describe processes wherein one mol of a THP compound and 0.02–0.2 mol of an amino-group-containing compound are condensed at 40°–120° C. in an aqueous or organic solvent system or in a melted state. But at such low temperatures under ordinary pressure, when the amino-group-containing compound is less than 0.05 mol, the condensation does not proceed. The use of more than 0.1 mol of said compound accelerates the condensation by co-condensation and reduces the disagreeable odor, and the co-condensation gives condensation products having a high fixing ability. However, not only the hand will be then stiffened by an increase in crosslinking density on the fiber, but also the flame retardant effect and its durability will be lowered by a drop in phosphorus content due to the co-condensation and a drop in resistance to hydrolysis.

The present invention relates to a process for the synthesis of water-soluble phosphorus-containing condensation products having a molar ratio P—CH$_2$—P linkage/P—CH$_2$OCH$_2$—P linkage of 0.8–4.0, wherein a THP compound is condensed by dehydration and deformaldehydation reactions by heating it under reduced pressure under acid conditions in a melted state and if desired in the presence of a catalyst of an amino-group-containing compound. The invention also relates to said products and to a process for the flame retardant treatment of textile articles by using said products.

An object of the present invention is to provide a water-soluble phosphorus-containing condensation product composed mainly of phosphonium groups which has a high content of phosphorus and a high flame retardant effect per unit weight of the condensation product and which is excellent in fixing ability.

Another object of the present invention is to provide a water-soluble phosphorus-containing condensation product having no characteristic disagreeable odor due to low molecular phosphines.

A further object of the present invention is to provide a water-soluble phosphorus-containing condensation product condensed by methylene linkages which has an excellent stability against hydrolysis and which can be easily insolubilized three-dimensionally with a small amount of a fixing agent and therefore, when applied to textile articles, has a small change in physical properties and in hand.

Other objects and effects will become apparent from the following description.

The present invention is characterized in that a THP compound is condensed by being heated at high temperatures in a melted state under reduced pressure under acid conditions. The THP compound, when heated at a relatively low temperature, for example at 130°–140° C., condenses even under reduced pressure by their linkages due to a dehydration condensation reaction and forms a methylene ether-type condensation product (A) as shown in formula (I), but when heated at a high temperature, especially above 150° C., the THP compound releases formaldehyde by a partial decomposition reaction, thus forming a reactive species (B) by the formula (II). Under ordinary pressure, the decomposition further proceeds such that the reaction (III) forming hydroxymethylphosphine (C) becomes predominant, but under a reduced pressure, especially below 100 mmHg, the reactive species (B) and another THP molecule seem to react with each other, condensing with the phosphonium group being included, to form a condensation product (D) of methylene linkage type shown by the formula (IV).

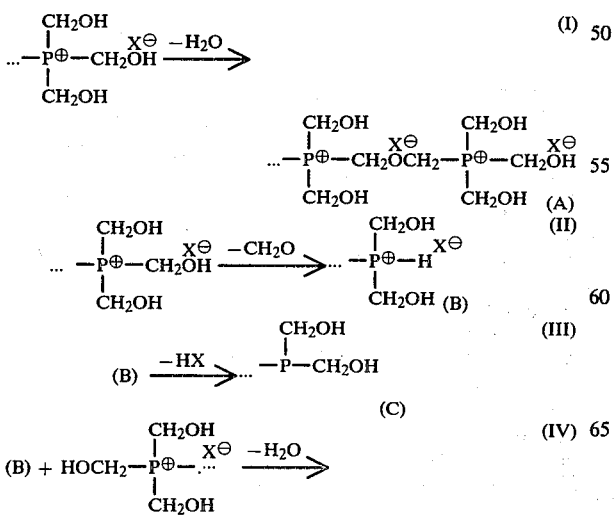

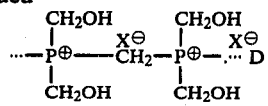

This methylene linkage type condensation product has a high phosphorus content and is excellent in resistance to hydrolysis. Moreover, we have found that, since the condensation product contains highly reactive hydroxymethyl groups linked to phosphonium groups, it can be easily insolubilized on fibers with a small amount of a fixing agent, e.g. the aminoplast precondensate. In flame retardant treatment of fibers, it is usual that a phosphorus-containing condensation product is fixed on fibers in combination with the aminoplast precondensate and then subjected to an oxidation treatment. The content of phosphorus per repeating structural unit of the resulting condensation product is 25.4% with the methylene ether type condensation product.

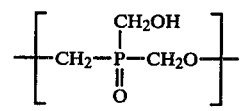

and 33.7% with the methylene type condensation product

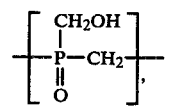

the maximum value being obtained in the case of the methylene type condensation. Therefore, the flame retardant effect can be markedly elevated by the methylene type condensation. In the present invention, condensation products having a molar ratio P—CH$_2$—P linkage/P—CH$_2$OCH$_2$—P linkage of 0.8–4.0, preferably 1.0–2.0 are produced, said ratio being measured from the area intensities of the peaks at 1.7 δppm (P—CH$_2$—P linkage proton) and 4.3 δppm (P—CH$_2$OCH$_2$—P linkage proton) by means of NMR (nuclear magnetic resonance) spectrum in D$_2$O. Condensation products having a molar ratio less than 0.8 are poor in resistance to hydrolysis, and moreover require a large amount of a fixing agent to obtain durable flame retardancy, this being a cause of a stiff hand and a decrease in strength. Condensation products having a molar ratio between said linkages of above 4 are not only impractical because they require high temperatures but also they cause gellation under certain conditions. To obtain desired condensation products, it is necessary, in the case of a THP compound alone, to heat to a temperature above 150° C. under reduced pressure, but since the addition of a small amount of an amino-group-containing compound can remarkably accelerate the condensation reaction, it is possible to reduce the lower limit of the heating temperature to a temperature exceeding 120° C. Although a clear account has not yet been given of the reason why amino-group-containing compounds can accelerate the condensation reaction, it is supposed that amino-group-containing compounds or their heat decomposition products may accelerate the deformaldehydation reaction. Addition of too large amount of an amino-group-containing compound causes co-condensation with the THP compound, thus lowering the phosphorus content in the resulting condensation product. This not only lowers the flame retardant effect but also causes too high a density of three-dimensional cross-linkage which remarkably stiffens the hand. The condensation products obtained in the present invention do not emit the disagreeable odor due to low molecular phosphines because by-produced phosphines are also sufficiently condensed.

Among the tetrakis(hydroxymethyl)phosphonium compounds used in the present invention, there may be exemplified tetrakis(hydroxymethyl)phosphonium chloride (hereinafter abbreviated as THPC), tetrakis(hydroxymethyl)phosphonium bromide, tetrakis(hydroxymethyl)phosphonium phosphate, tetrakis(hydroxymethyl)phosphonium acetate (hereinafter abbreviated as THPA), tetrakis(hydroxymethyl)phosphonium sulfate, tetrakis(hydroxymethyl)phosphonium oxalate, etc. Among these, THPC and THPA are particularly preferable. The THP compounds may be used as a mixture of two or more compounds. Also, a small amount of tris(hydroxymethyl)phosphine may be mixed under certain conditions.

Among the amino-group-containing compounds used for accelerating the condensation of the THP compounds, there may be exemplified triazines such as melamine, N-alkylmelamines, ammeline, formoguanamine, acetoguanamine, benzoguanamine; urea or thiourea and their derivatives such as N-alkylureas, N-arylureas; cyclic ureas such as ethyleneurea, propyleneurea, triazone, urone, 4,5-dihydroxyethyleneurea; and cyanamide, dicyandiamide, guanidine, guanylurea, alkylcarbamate, aliphatic amides, aromatic amides, biuret, alkylenediamine, etc. Among these, ethyleneurea, guanidine, melamine, urea and dicyandiamide are preferable and dicyandiamide is particularly preferable.

The amount of addition of an amino-group-containing compound in the condensation of a THP compound depends on the desired properties of the resulting condensation product, the type of the amino-group-containing compound to be used, etc. But usually 0.001–0.02 mol of an amino-group-containing compound per mol of a THP compound is preferable, and 0.005–0.015 mol is particularly preferable. With an amount less than 0.001 mol, there is no accelerating action for condensation. As the amount exceeds 0.02 mol, the hand of the treated cloth becomes gradually stiff. As the amount exceeds 0.2 mol, not only the hand becomes stiff but also the flame retardant effect becomes gradually lowered. However, when the desired flame retardancy is of a slight degree or a stiff hand is required, it is possible to use about 0.4 mol of an amino-group-containing compound.

The condensation of a THP compound is carried out under heating in a melted state under reduced pressure in the absence of a diluent such as water or an organic solvent. At this time, the pH of the reaction system measured as a 80% aqueous solution should be normally below 7, preferably below 4. In the event that this pH is about 7, there is a danger of explosion accompanied by an exothermic decomposition reaction of the condensation product. In the condensation of a THP compound,, the use of a Lewis acid catalyst such as magnesium chloride or zinc nitrate, etc. is not necessary because the compound itself has a catalytic effect. However, in some cases, the addition may be preferable depending upon the composition of the reaction system. The degree of reduced pressure should be normally below 100 mmHg, preferably 10–100 mmHg, more preferably 30–70 mmHg. At this time, the atmosphere may be replaced with an inert gas. As regards the reaction temperature when condensing a THP compound singly, a temperature exceeding 150° C. is necessary, and a temperature between 151° and 180° C. is preferable. In the condensation using an amino-group-containing compound together, even a low temperature normally in excess of 120° C. may be used, although the temperature depends on the type of said compound, since the condensation of the THP compound is then remarkably accelerated. A temperature between 135° and 160° C. is preferable and a temperature between 150° and 155° C. is particularly preferable. The reaction time should be normally 30 minutes to 5 hours, preferably 30 minutes to 3 hours, although the time depends on the type of the amino-group-containing compound to be used together and the temperature. Under these conditions, a water-soluble phosphorus-containing condensation product having a molar ratio P—$CH_2$—P linkage/P—$CH_2OCH_2$—P linkage of 0.8–4.0, preferably 1.0–2.0 is synthesized. If desired, said condensation product can be further partially or completely etherified at its free hydroxyl groups with an alcohol having 1 to 4 carbon atoms. Furthermore, if desired, said water-soluble, phosphorus-containing condensation product can be partially or completely changed into its corresponding hydroxide with a strong base, for example an alkali hydroxide. It is preferable that the specific viscosity of a 40% aqueous solution of the water-soluble phosphorus-containing condensation products, measured at 30° C., should be 2–7.

The thus obtained water-soluble, phosphorus-containing condensation product is then applied to textile articles together with the aminoplast precondensate, and is then fixed by the wet-fixing method, ammonia-fixing method or heat-fixing method. The latter method is convenient in most cases. If desired, an amino compound which can be methylolated may be used together in the treating liquid.

The aminoplast precondensate to be used is the precondensation product having at least one methylol group or alkoxymethyl group in the molecule. Mono- or poly-methylol compounds of amino compounds such as melamine, alkyleneureas, urea, thiourea, uron, triazones, carbamates, guanylurea, 4,5-dihydroxyethyleneurea, $\beta,\beta',\beta''$-nitrilotrispropionic acid amide, etc. and their lower alcohol etherified compounds may be exemplified. Among these, polymethylolated compounds or polymethoxymethylolated compounds of melamine are particularly preferable. Among the methylolatable amino compounds that may be used together in the treating liquid, there may be exemplified urea, thiourea, dicyandiamide, guanylurea, guanidine carbonate, guanidine phosphate, guanidine hydrochloride, formamide, sulfonylamide, dialkylphosphorylamide, cyanamide, biuret, etc. Among these urea is particularly preferable.

As regards the compounding ratio of (1) the above-mentioned water-soluble phosphorus-containing condensation product (hereinafter referred to as phosphonium oligomer), (2) the aminoplast precondensate and (3) a methylolatable amino compound, (1):(2)+(3) should be normally 70:30 to 95:5, preferably 80:20 to 90:10 by weight as active ingredients, and (2):(3) should be normally 95:5 to 5:95, preferably 50:50 to 25:75 by weight as active ingredients.

A method for the preparation of a flame retardant treatment liquid for fibers is exemplified in the following: A liquid is prepared which consists of a phosphonium oligomer, the precondensation product of an aminoplast, and if desired, mixed with a methylolatable amino compound. To this liquid, if desired, a softening agent, antistatic agent, soil releasing agent, etc. may be added, and the pH of the liquid is preferably adjusted to 4 to 8 with a base such as sodium hydroxide, potassium hydroxide, sodium carbonate, etc.

Another flame retardant, for example tris(2,3-dibromopropyl)phosphate, polyvinyl bromide, tetrabromobisphenol A-containing polyester or polyether, poly(2,3-dibromopropyl)acrylate, etc. or their emulsion, Pyrovatex CP (Ciba Geigy; methylolated dialkylphosphonopropionamide), Pyrovatex 3887 (Ciba Geigy; brominated hydrocarbon), Fyrol 76 (Stauffer Chemical; vinylphosphonate oligomer), FRP-44 (White Chemical; decabromodiphenyl ether+$Sb_2O_3$), ANTI-BLAZE 19 and 19-T Flame Retardant (Mobil Chem; alkyl phosphonate) may be used together in the same bath, or may be used before or after the treatment with the phosphonium oligomer of the present invention, whereby the flame retardancy and contigently the hand can be improved to a further extent.

The treating liquid thus prepared is then applied to textile articles by spraying, padding, coating, liquid transferring, etc. and thereafter, in a preferred heat-fixing method, the treated articles are normally heat-treated after drying. The drying conditions are not particularly limited but drying usually at 70°–110° C. for 3–10 minutes is convenient. The heat fixing conditions are usually 120°–200° C. for 10 seconds to 30 minutes. Of course, a shorter time is sufficient for a higher temperature. The amount of application of the phosphonium oligomer depends on the kind and weight of the textile articles to be treated, the degree of desired flame retardancy, the presence of another flame retardant to be used in combination, and its kind and amount, but it is normally 10 to 90 weight percent, preferably 20 to 70 weight percent, based on the fiber weight. The textile articles after heat treatment are rinsed with water and dried preferably after oxidation treatment.

The textile articles to be flame retardant treated include natural or regenerated cellulose fibers, such as cotton, hemp, viscose rayon, cuprammonium rayon, polynosic rayon; protein fibers such as wool, silk, furs; semi-synthetic fibers such as cellulose acetate, protein-acrylonitrile graft-copolymer fiber; synthetic fiber such as polyester, polyamide, polyacrylonitrile; various property-modified fibers such as antistaticity-modified synthetic fibers, flame retardancy-modified synthetic fibers, dye-affinity-modified synthetic fibers, which have been property-modified at any step in fiber production, and fiber masses, yarns, knit or woven fabrics, non-woven fabrics, carpets or rugs produced from these fibers and mixtures. The flame retardant effect according to the present invention is very striking when it is applied to a mixture of non-meltable fibers and meltable fibers, such as cellulose fibers and polyester fibers, which are usually difficult to be flame retardant processed, and particularly when the ratio of the two is 1:4 to 4:1. Said flame retardant is also effective for wood, paper, leather, and synthetic resin films. It can be used not only as a flame retardant but also as a hand improving agent.

The present invention is explained hereinafter by way of examples. In the examples parts and percentages are by weight unless otherwise specified.

EXAMPLES 1 TO 14: SYNTHESIS OF PHOSPHONIUM OLIGOMERS

Example 1

Figure 2:
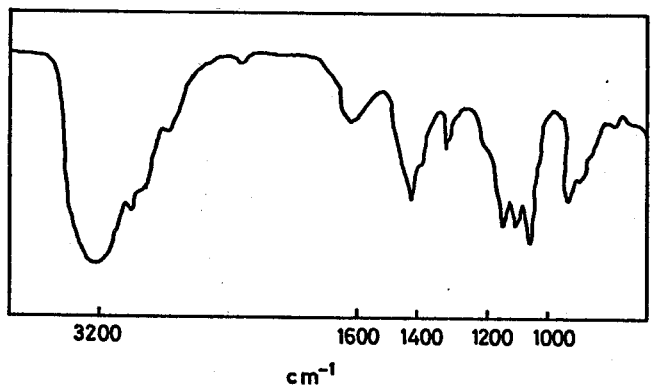

1500 g. of 80% THPC (pH 0.8) was put into a two-liter four-mouthed flask equipped with a reduced pressure distillation apparatus, a thermometer and a stirrer, and the external temperature was heated to about 100° C. under a reduced pressure of 60 mm Hg to remove water contained in the THPC. The inner temperature was then raised to 155° C. under the same degree of reduced pressure and was maintained at this temperature about 60 minutes. During this time, a mixed solution was distilled out which contained water and formaldehyde resulting from dehydration and deformaldehydation reactions and a slight amount of hydrochloric acid resulting from a decomposition reaction. After the contents of the flask were cooled, an amount of water was added to the non-flowable resinous substance thus obtained to make it up to a 80% aqueous solution. The pH of this solution was 1.5. The specific viscosity ($\eta_{sp}$) of a solution obtained by diluting this 80% aqueous solution with the same amount of water, as measured at 30° C. with an Ostwald viscosimeter, was 2.8. The solution did not substantially emit the disagreeable odor resulting from low molecular phosphines, and thus there was no problem of odor during handling or treatment. In FIG. 1 is shown the result of measurement of the NMR spectrum of the thus-obtained condensation product in $D_2O$. In this figure, the two peaks at 1.7 δppm were identified as P—$CH_2$—P linkage methylene proton, the peak at 4.3 δppm as P—$CH_2$—O—$CH_2$—P linkage methylene proton and the peak at 4.7 δppm as proton of P—$CH_2OH$ and $H_2O$. The molar ratio P—$CH_2$—P linkage/P—$CH_2OCH_2$—P linkage found from the area intensities at the peaks of 1.7 δppm and 4.3 δppm was 1.1. The stability upon storage of the condensation product was good. The infrared spectrum of the condensation product is shown in FIG. 2. When an aqueous solution of sodium lauryl sulfate was added to this condensation product, a precipitate was formed, and therefore high molecular cationic properties were confirmed.

Example 2

A condensation product was produced under the same conditions as in Example 1 except that the condensation was carried out at 155° C. for 80 minutes. The $\eta_{sp}$ of a 40% aqueous solution was 6.65. The molar ratio P—$CH_2$—P linkage/P—$CH_2OCH_2$—P linkage was 1.15.

Example 3

238 g. (1 mol) of 80% THPC and 0.42 g. (0.005 mol) of dicyandiamide (the pH of the reaction system was 0.8) were put in a one-liter four-mouthed flask equipped with a reduced pressure distillation apparatus, a thermometer and a stirrer, and the reduction solution was heated to about 100° C. under a reduced pressure of 30 mm Hg to remove water. The solution was then heated to 145° C. under a reduced pressure of 30 mm Hg to accomplish condensation. At this time, formaldehyde and water resulting from dehydration and deformaldehydation reactions were distilled out. After about one hour, the heating was stopped and after cooling the reaction system was made up to a 80% aqueous solution by adding water. The pH of the thus-obtained 80% aqueous solution was 1.5 and the $\eta_{sp}$ of a 40% aqueous solution was 2.1. The molar ratio P—CH$_2$—P linkage/P—CH$_2$OCH$_2$—P linkage was 1.3.

Example 4

238 g. (1 mol) of 80% THPC and 0.84 g. (0.01 mol) of dicyandiamide were condensed by heating at 155° C. under a reduced pressure of 60 mm Hg for one hour in the same way as in Example 3. The pH of a 80% aqueous solution of the condensation product was 1.3. The $\eta_{sp}$ of a 40% aqueous solution was 3.0. The molar ratio of P—CH$_2$—P linkage/P—CH$_2$OCH$_2$—P linkage was 1.7. After storage for three months, the solution was stable and did not change its solubility, viscosity, processability and flame retardancy, and there was no substantial emission of the disagreeable odor from the solution.

Example 5

A mixture of 238 g. (1 mol) of 80% THPC and 0.84 g. (0.01 mol) of dicyandiamide (the pH of the mixture was 0.8) was condensed by heating at 135° C. under a reduced pressure of 30 mm Hg for 3 hours in the same way as in Example 3. The pH of a 80% aqueous solution of the condensation product was 1.4, the $\eta_{sp}$ of a 40% aqueous solution was 3.5 and the molar ratio P—CH$_2$—P linkage/P—CH$_2$OCH$_2$—P linkage was 1.1.

Example 6

238 g. of 80% THPC and 16.8 g. (0.2 mol) of dicyandiamide were condensed by heating in the same way under the same conditions as in Example 3. The pH of a 80% aqueous solution of the condensed product was 1.5, and the $\eta_{sp}$ of a 40% aqueous solution was 3.3. The molar ratio P—CH$_2$—P linkage/P—CH$_2$OCH$_2$—P linkage of the condensation product was 0.8. This low value is supposed to have resulted from the introduction of P—CH$_2$—N— linkage due to the co-condensation of THPC and dicyandiamide.

Example 7

238 g. (1 mol) of 80% THPC and 1.43 g. (0.015 mol) of guanidine hydrochloride (the pH of the reaction liquid was 0.5) were put in a one-liter four-mouthed flask and the reaction mixture was heated to about 80° C. under a reduced pressure of 40–70 mm Hg, and while the reaction system was dehydrated the temperature was raised to 135° C. Further, the reaction mixture was condensed by heating at 135° C. under a reduced pressure of 30 mm Hg. After about 3 hours, the heating was stopped, and after cooling the resulting solution of the condensation product was made up to a 80% aqueous solution by adding water. The pH of the 80% aqueous solution of the condensation product was 1.5, the $\eta_{sp}$ of a 40% aqueous solution was 2.5, and the molar ratio of P—CH$_2$—P linkage/P—CH$_2$OCH$_2$—P linkage was 1.2. The aqueous solution even after storage for three months showed excellent stability without any change in stability, viscosity, processability and flame retardancy, and it did not substantially emit the disagreeable odor.

Example 8

A mixed solution (pH 0.8) of 238 g. (1 mol) of 80% THPC and 0.96 g. (0.01 mol) of guanidine hydrochloride was condensed by heating at 155° C. under a reduced pressure of 60 mm Hg for one hour in the same way as in Example 3. The $\eta_{sp}$ of a 40% aqueous solution of the condensation product was 3.0 and the molar ratio P—CH$_2$—P linkage/P—CH$_2$OCH$_2$—P linkage was 1.4. There was no emission of the disagreeable odor.

Example 9

A mixed solution (pH 0.5) of 238 g. (1 mol) of 80% THPC and 0.6 g. (0.01 mol) of ethylenediamine was condensed by heating at 155° C. under a reduced pressure of 60 mm Hg for one hour in the same way as in Example 3. Aqueous solutions of the condensation product did not emit the disagreeable odor. The molar ratio P—CH$_2$—P linkage/P—CH$_2$OCH$_2$—P linkage was 1.3.

Example 10

238 g. (1 mol) of 80% THPC and 0.6 g. (0.01 mol) of urea were condensed by heating at 155° C. under a reduced pressure of 60 mm Hg for one hour in the same way as in Example 3. A 80% aqueous solution of the condensation product slightly emitted the disagreeable odor. The molar ratio P—CH$_2$—P linkage/P—CH$_2$OCH$_2$—P linkage of the condensation product was 1.3.

Example 11

A mixed solution (pH 0.5) of 238 g. (1 mol) of 80% THPC and 1.26 g. (0.01 mol) of melamine was condensed by heating at 155° C. under a reduced pressure of 60 mm Hg for one hour in the same way as in Example 3. The molar ratio P—CH$_2$—P linkage/P—CH$_2$OCH$_2$P linkage of the condensation product was 1.3 and a 80% aqueous solution thereof slightly emitted the disagreeable odor.

Example 12

238 g. (1 mol) of 80% THPC, 0.63 g. (0.005 mol) of melamine and 0.3 g. (0.005 mol) of urea were condensed by heating at 155° C. under a reduced pressure of 60 mm Hg for one hour in the same way as in Example 3. The molar ratio P—CH$_2$—P linkage/P—CH$_2$OCH$_2$—P linkage of the condensation product was 1.1. A 80% aqueous solution thereof slightly emitted the disagreeable odor.

Comparative Example 1

1500 g. of 80% THPC was put in a 2-liter four-mouthed flask equipped with a reduced pressure distillation apparatus. After water was removed as in Example 1, the contents of the flask were condensed by heating at 135° C. for three hours and 1080 g. of a condensation product was obtained. After cooling, the condensation product was in a liquid state. The pH of a 80% aqueous solution of the condensation product was 1.5, the $\eta_{sp}$ of a 40% aqueous solution thereof was 1.0 and the molar ratio P—CH$_2$—P linkage/P—CH$_2$OCH$_2$—P linkage was 0.4. The aqueous solution considerably emitted the disagreeable odor.

Comparative Example 2

1500 g. of 80% THPC and 1000 g. of m-xylene were put into a 3-liter four-mouthed flask equipped with a reflux condenser, an ordinary pressure distillation apparatus and a thermometer. Upon heating, when the inner temperature reached 120° C., the reaction mixture began to boil. As the water contained in the THPC was removed by azeotropy with xylene, the temperature of the reaction mixture was gradually raised to 135° C. By heating the reaction mixture at 135° C. for 9 hours, the water formed by dehydration reaction was removed. Thereafter, the contents of the flask were cooled to 90° C. and dissolved in 800 g. water. The whole was further cooled to room temperature to separate the aqueous solution from the xylene phase, and water was removed again under reduced pressure. After the water content in the obtained condensation product was measured by a Carl Fischer's water content measuring apparatus, the condensation product was made up to an accurate 80% aqueous solution, which was 1331 g. by weight. The solution emitted a markedly disagreeable odor, and at the same time, it irritated the eye strongly. This irritation is supposed to have been caused by a chloride of methaxylene.

The molar ratio P—CH$_2$—P linkage/P—CH$_2$OCH$_2$—P linkage of the condensation product was 0.2. The $\eta_{sp}$ of a 40% aqueous solution thereof was 0.85.

Comparative Example 3

1200 g. of crystalline anhydrous THPC was put into a 2-liter four-mouthed flask equipped with a stirrer, a thermometer and a gas introducing pipe. The THPC was condensed at 175° C. for 6 hours under ordinary pressure while nitrogen gas was blown into the flask at the rate of 60 ml./min. The flask was then cooled, and an amount of water was added to the resulting low-viscosity liquid to make up it to a 80% aqueous solution. The solution considerably emitted the disagreeable odor. The molar ratio P—CH$_2$—P linkage/P—CH$_2$OCH$_2$—P linkage of the condensation product was about 0.6 and the $\eta_{sp}$ of a 40% aqueous thereof was 2.0. When an aqueous solution of sodium lauryl sulfate was added to this condensation product, no precipitate was formed, and therefore high molecular cationic properties were not observed.

Comparative Example 4

238 g. (1 mol) of 80% THPC was put into a one-liter four-mouthed flask equipped with a reduced pressure distillation apparatus. After water was removed in the same way as in Example 1, the pressure was returned to atmospheric pressure and the inner temperature was raised to 155° C. by heating. Condensation was further carried out at 155° C. for one hour. Thereafter, the resulting condensation product was made up to a 80% aqueous solution with water. The solution did not substantially emit the disagreeable odor. The $\eta_{sp}$ of a 40% aqueous solution of the condensation product was 1.0, and this shows that the condensation did not proceed.

Comparative Example 5

238 g. (1 mol) of 80% THPC and 4.2 g. (0.05 mol) of dicyandiamide were put into a one-liter four-mouthed flask equipped with a reduced pressure distillation apparatus. After water was removed in the same way as in Example 1, the pressure was retured to atmospheric pressure, and the inner temperature was raised to 135° C. by heating. Thereafter, the contents of the flask were further condensed by heating to 135° C. for about three hours. Then an amount of water was added to the condensation product to make up to a 80% aqueous solution. The solution emitted no substantial disagreeable odor. The $\eta_{sp}$ of a 40% aqueous solution of the condensation product was 1.3, and this shows that the condensation did not substantially proceed.

Comparative Example 6

One mol of 80% THPC neutralized to a pH of 7.2 beforehand with a 20% aqueous solution of sodium hydroxide was put into a one-liter four-mouthed flask equipped with a stirrer, a thermometer and a reduced pressure distillation apparatus. The outer temperature of the flask was raised to about 70° C., and under a reduced pressure of 10–20 mm Hg, water was sufficiently removed. Thereafter, 160 g. xylene and 3.81 g. magnesium chloride were added, and while the contents were boiled (at about 135° C.) under atmospheric pressure, the water formed was removed azeotropically. After about three hours of condensation, the solvent was distilled off. The $\eta_{sp}$ of a 40% aqueous solution of the condensation product was 1.2, and this shows that the condensation did not substantially proceed.

Comparative Example 7

Into the flask used in Comparative Example 6, a mixture of 1 mol of 80% THPC neutralized to a pH of 7.2 beforehand with a 20% aqueous solution of sodium hydroxide and 3.81 g. of magnesium chloride, was charged. Under a reduced pressure of 60 mm Hg, the external temperature of the flask was raised to about 100° C. to remove water. Thereafter, when the temperature was further raised to 130° C., the reaction mixture caused an exothermic decomposition reaction. The internal temperature rose sharply to make temperature control impossible and finally the contents exploded. The gas formed by explosion caught fire upon contact with air and burned.

The results obtained in Examples 1–12 and Comparative Examples 1–7 are summarized in Table 1.

Table 1

| | | Conditions of condensation | | | | Properties of condensation product | | |
|---|---|---|---|---|---|---|---|---|
| | | Amino-group-containing compound | | Degree of reduced pressure (mm Hg) | Temp. (° C.) | Time (hrs.) | Viscosity* $\eta$sp (c = 40%) | P—CH$_2$—P/ P—CH$_2$OCH$_2$—P (molar ratio) | Odor (garlic-like odor) |
| | | Kind | Mols per mol of THPC | | | | | | |
| Ex. | 1 | — | 0 | 60 | 155 | 1.0 | 2.8 | 1.1 | slight |
| " | 2 | — | 0 | 60 | 155 | 1.33 | 6.7 | 1.15 | " |
| " | 3 | dicyandiamide | 0.005 | 30 | 145 | 1.0 | 2.1 | 1.3 | substantially none |
| " | 4 | " | 0.01 | 60 | 155 | 1.0 | 3.0 | 1.7 | " |
| " | 5 | " | 0.01 | 30 | 135 | 3.0 | 3.5 | 1.1 | " |
| " | 6 | " | 0.20 | 60 | 155 | 1.0 | 3.3 | 0.8 | " |
| " | 7 | guanidine HCl | 0.015 | 30 | 135 | 3.0 | 2.5 | 1.2 | " |
| " | 8 | " | 0.01 | 60 | 155 | 1.0 | 3.0 | 1.4 | " |
| " | 9 | ethylene diamine | 0.01 | 60 | 155 | 1.0 | 2.8 | 1.3 | " |

Table 1-continued

| | | Conditions of condensation | | | | | Properties of condensation product | | |
|---|---|---|---|---|---|---|---|---|---|
| | | Amino-group-containing compound | | Degree of | | | | | |
| | | Kind | Mols per mol of THPC | reduced pressure (mm Hg) | Temp. (°C.) | Time (hrs.) | Viscosity* ηsp (c = 40%) | P—CH$_2$—P/ P—CH$_2$OCH$_2$—P (molar ratio) | Odor (garlic-like odor) |
| " | 10 | urea | 0.01 | 60 | 155 | 1.0 | 2.9 | 1.3 | slight |
| " | 11 | melamine | 0.01 | 60 | 155 | 1.0 | 2.8 | 1.3 | " |
| " | 12 | melamine and urea | 0.005 0.005 | 60 | 155 | 1.0 | 2.8 | 1.3 | " |
| Comp. Ex. | 1 | — | 0 | 30 | 135 | 3.0 | 1.0 | 0.4 | considerable |
| " | 2 | — | 0 | atm. pr. in the presence of xylene | 135 | 9.0 | 0.85 | 0.2 | remarkable |
| " | 3 | — | 0 | atm. pr. in the presence of an inert gas | 175 | 6.0 | 2.0 | 0.6 | considerable |
| " | 4 | — | 0 | atm. pr. | 155 | 1.0 | 1.0 | not condensed | substantially none |
| " | 5 | dicyandiamide | 0.05 | atm. pr. | 155 | 3.0 | 1.3 | almost not condensed | " |
| " | 6 | (neutralized to pH 7.2) | 0 | atm. pr. | 135 | 3.0 | 1.2 | " | remarkable |
| " | 7 | " | 0 | 60 | 155 | — | — | exploded | — |

*30° C. Ostwald viscosimeter.

As apparent from Table 1, the condensation products obtained by the process of the present invention have a large proportion of methylene linkage, and in comparison with condensation products obtained under atomospheric pressure, they have a higher degree of condensation. Moreover, because they scarcely emit the disagreeable odor due to low molecular weight phosphines, the problem of the disagreeable odor upon processing textile articles and in processed articles has been solved.

The results of elemental analysis of the condensation products obtained in Example 1, Example 2 and Comparative Example 3 are shown in Table 2.

Table 2

| | Ex. 1 | Ex. 2 | Comp. Ex. 3 | THPC (calculated taking experimental data as 100%) |
|---|---|---|---|---|
| P % | 19.9 | 20.5 | 24.4 | 16.3 |
| ionic Cl % | 12.0 | 12.5 | 1.6 | 19.3 |

It is seen from Table 2 that the condensation products obtained according to the present invention are completely different in composition from the condensation product of Comparative Example 3. This shows that, in the case of the condensation products of the present invention produced under reduced pressure, the condensation occurs with reactive phosphonium groups being kept remaining, while the condensation product produced at atmospheric pressure under the introduction of an inert gas is liable to form phosphines by decomposing phosphonium groups.

The results of measurement of material balance in the condensation reaction of Example 1 and Comparative Examples 2 are shown in Table 3.

Table 3

| | Example 1 | Comparative Example 2 |
|---|---|---|
| Amount of THPC charged (g.) | 1500 | 1500 |
| Amount of condensation product formed (g.) | 1005 | 1066 |
| Amount of volatile substances during condensation reaction (g.) | 495 | 434 |
| Free water contained in THPC (g.) | 300 | 300 |
| Water formed by condensation (g.) | 102 | 127 |
| Formaldehyde, hydrogen chloride and others released during condensation (g.) | 93 | 7 |

It is seen from the molar ratio P—CH$_2$—P linkage/P—CH$_2$OCH$_2$—P linkage in Table 1 and the results in Table 3 that the condensation in the present invention proceeds by dehydration and deformaldehydation reactions, while in the comparative example nearly only dehydration reaction takes place.

The difference resulting from the forms of condensation under reduced pressure and atmospheric pressure is obvious from the comparison between Comparative Example 6 and Comparative Example 7. Namely, in the condensation of tetrakis(hydroxymethyl)phosphonium hydroxide (which is liable to decomposition) formed by the neutralization of THPC, the reaction cannot be controlled under reduced pressure because an exothermic decomposition reaction occurs, but in the presence of xylene the reaction is not accompanied by the exothermic decomposition reaction.

EXAMPLE 13

A self-condensed product of THPC was synthesized under a reduced pressure of 30 mm Hg at 135° C. to 175° C. in the same way as in Example 1. The molar ratio P—CH$_2$—P linkage/P—CH$_2$OCH$_2$—P linkage and the $\eta_{sp}$ of a 40% aqueous solution of the condensation product thus obtained are shown in Table 4.

Table 4

Relation between condensation conditions and properties of condensation products.

| Condensation conditions | | THPC only | | | | THPC : dicyandiamide = 1 : 0.01 mol | | | |
|---|---|---|---|---|---|---|---|---|---|
| | | | | Disagreeable odor* | | | | Disagreeable odor* | |
| Temp. (°C.) | Time (hrs) | $\eta_{sp}$ | P—CH$_2$—P/ P—CH$_2$OCH$_2$—P | pH 1.5 | pH 5 | $\eta_{sp}$ | P—CH$_2$—P/ P—CH$_2$OCH$_2$—P | pH 1.5 | pH 5 |
| 115 | 5 | — | — | — | — | 1.1 | did not condense | — | — |
| 135 | 3 | 2.5 | 0.4 | | | 2.6 | 1.1 | × | ×-Δ |
| 145 | 3 | 3.0 | 0.6 | Δ | | — | — | — | — |
| 155 | 1 | 2.5 | 1.1 | × | Δ | 2.8 | 1.8 | × | × |
| 165 | 1 | 4.5 | 1.6 | × | ×-Δ | — | — | — | — |
| 175 | 1 | gelled | — | — | — | gelled | — | — | — |

\* remarkable
considerable
Δslight
×none

The condensation products obtained by the process of the present invention have no disagreeable odor due to low molecular weight phosphine, and even when adjusted to a pH of 5, they do not smell, or only slightly smell, so that the problem of the odor during handling has been solved.

EXAMPLE 14

275 g. (1 mol) of 80% THPC and 0.6 g. (0.01 mol) of urea were condensed in the same way as in Example 3 by heating at 145° C. under a reduced pressure of 60 mm Hg for one hour. The molar ratio P—CH$_2$—P linkage/P—CH$_2$OCH$_2$—P linkage of the condensed product was 1.1 and the $\eta_{sp}$ of a 40% aqueous solution thereof was 2.8.

EXAMPLE 15

A blend-spun broad cloth of polyester/cotton (65/35) was padded with a treating liquid of the following composition. After the cloth was squeezed to a wet pickup of 90%, it was dried at 80° C. for 10 minutes and heat-treated at 160° C. for three minutes.

Treating liquid:

| | |
|---|---|
| Phosphonium oligomer (80% aqueous solution) adjusted to a pH of 5–5.5 with an aqueous solution of sodium hydroxide) | 55 parts |
| Sumitex Resin M-3 (80% aqueous solution) (Sumitomo Chemical Co. Ltd.; trimethoxymethylmelamine) | 13 parts |
| Liponox NA (Lion Fat and Oil Co. Ltd.; nonionic wetting agent) | 0.1 part |

Treating liquid:
-continued

| | |
|---|---|
| Water | balance |
| Total | 100 parts |

The treated cloth was then subjected to an oxidation treatment in an aqueous solution consisting of 60 g/l. of a 30% aqueous solution of hydrogen peroxide and 2 g/l. of sodium carbonate at 40° C. for 20 minutes and it was rinsed with water and dried. The percent phosphorus content, flame retardancy, and stiffness of this cloth were evaluated by the following testing methods. The results are shown in Table 5.

Testing methods:
(1) Flame retardancy
   Char length (cm.) according to DOCFF 3-71. Average value for 5 test pieces in warp direction. If one test piece is completely burned, this cloth is rated as BEL (burned entire length).
(2) Percent phosphorus content
   Colorimetric quantitative determination by molybdic acid.

$$\text{Percent retention} = \frac{\text{Phosphorus content after washing}}{\text{Phosphorus content before washing}} \times 100$$

(3) Stiffness (mm.) in warp direction
   JIS L 1004 5-17 A Method (cantilever method).

Percent increase in stiffness
$$= \frac{\text{Stiffness of treated cloth} - \text{Stiffness of untreated cloth}}{\text{Stiffness of untreated cloth}} \times 100$$

(4) Washing
   JIS L 1042 F-2 Method

Table 5

| Experiment No. | Present invention | | | | | | | | | | | | Comparatiive Example | | | | | Un-treated |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | |
| Phosphonium oligomer Example | 1 | 2 | 3 | 4 | 5 | 6 | 7 | 8 | 9 | 10 | 11 | 12 | | | | | | |
| Comparative Example | | | | | | | | | | | | | 1 | 2 | 3 | 4 | 5 | |
| Disagreeable odor Treating liquid | sl | sl | no | no | no | no | no | no | no | no | no | no | c | r | r | sl | sl | |
| Upon treatment Flame | no | no | no | no | no | no | no | no | no | no | no | no | c | c | c | no | no | |

Table 5-continued

| Experiment No. | Present invention | | | | | | | | | | | | Comparatiive Example | | | | | Un-treated |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | |
| retardancy (cm.) Before washing | 10.1 | 9.0 | 10.1 | 10.5 | 10.8 | 9.9 | 10.5 | 8.0 | 8.1 | 8.0 | 8.0 | 8.3 | 10.5 | 11.4 | BEL | BEL | BEL | BEL |
| After 20 washings | 11.1 | 10.5 | 11.0 | 10.7 | 13.0 | 17.3 | 13.0 | 9.0 | 9.0 | 9.5 | 9.0 | 10.0 | 18.0 | BEL | BEL | BEL | BEL | BEL |
| Percent phosphorous content Before washing | 4.0 | 4.3 | 4.0 | 4.0 | 4.1 | 4.0 | 4.0 | 4.2 | 4.2 | 4.3 | 4.2 | 4.3 | 3.6 | 3.0 | 0.24 | 2.0 | 2.0 | |
| After 20 washings | 3.2 | 3.5 | 3.1 | 3.2 | 3.0 | 2.6 | 3.1 | 3.4 | 3.4 | 3.5 | 3.4 | 3.4 | 2.5 | 2.0 | 0.15 | 1.2 | 1.3 | |
| Percent retension | 80 | 81 | 78 | 80 | 73 | 65 | 78 | 81 | 81 | 80 | 81 | 80 | 69 | 67 | 63 | 60 | 65 | |
| Hand Stiffness (mm.) | 68 | 75 | 72 | 73 | 71 | 95 | 71 | 71 | 70 | 71 | 71 | 70 | 70 | 70 | 63 | 60 | 61 | 37 |
| % increase in stiffness | 84 | 103 | 95 | 97 | 92 | 157 | 92 | 92 | 89 | 92 | 92 | 89 | 89 | 89 | 70 | 62 | 65 | | sl = slight
c = considerable
r = remarkable

The phosphonium oligomers of the present invention did not emit the disagreeable odor and gave flame retardancy having excellent washing durability. But the oligomers obtained by adding a relatively large amount of dicyandiamide not only gave a considerably stiff hand but also showed a tendency of reducing the washing durability. On the other hand, the oligomers in Comparative Examples 1–3 not only emitted the disagreeable odor during treatment, thus causing a problem in environmental hygenics, but also the flame retardancy after 20 washings thereof was unpassable. The condensation products in Comparative Examples 4 and 5 did not substantially emit the disagreeable odor but gave poor flame retardancy.

EXAMPLE 16

A blend-spun shirting (45's×14's/91×85) of polyester/cotton (65/35) was padded with a treating liquid of the following composition. After the shirting was squeezed to a wet-pickup of 108%, it was dried at 80° C. for 7 minutes and heat-treated at 160° C. for three minutes.

| Treating liquid: | |
|---|---|
| Phosphonium oligomer obtained in Example 1 (80% aq. soln.) (adjusted to a pH of 5.2 with a 20% aq. solution of sodium hydroxide) | 66 parts |
| Urea | x parts |
| Sumitex resin M-3 | y parts |
| Polyethylene glycol (MW = 600) | 2 parts |
| Eleganol SRT-1 (Meisei Chemical Co.; fatty acid ester type softener) | 2 parts |
| DIC Silicone Softener-TS (Dainippon Ink Mfg. Co.; dimethylpolysiloxane type softener) | 0.5 part |
| Liponox NA | 0.1 part |
| Water | balance |
| Total | 120 parts |

After the cloth was subjected to oxidation treatment, it was rinsed with water and dried. The percent phosphorus content, the flame retardancy and the hand by means of a Handl-o-meter (measuring 10×10 cm. (warp×weft) test pieces at a slit width of one cm.; JIS L-1004 17-E Method) of the cloth thus treated were evaluated and the results in Table 6 were obtained.

Table 6

| | Experiment No. | Present invention | | | | | Un-treated |
|---|---|---|---|---|---|---|---|
| | | 18 | 19 | 20 | 21 | 22 | |
| Recipe (parts) | Urea | — | 2 | 4 | 6 | 6 | — |
| | Sumitex resin M-3 | 13 | 5 | 4 | 2 | — | |
| Flame retardancy* (cm) | Before washing | 9.5 | 9.5 | 9.4 | 9.6 | 9.6 | BEL |
| | After 50 washings** | 10.8 | 10.8 | 10.8 | 9.1 | 17.9 | BEL |
| Hand | Handl-o-meter (g.) | 108 | 91 | 63 | 67 | 51 | 30 |
| % P content | Before washing | 5.09 | 5.10 | 4.98 | 5.12 | 4.99 | |
| | After 50 washings** | 4.07 | 3.93 | 3.81 | 3.97 | 3.61 | |
| | % retension | 77 | 77 | 77 | 78 | 72 | |

*DOCFF 3-71
**AATCC 124 III B Method

It is seen from the data in Table 6 that Experiment Nos. 20 and 21 gave a particularly good hand and high flame retardancy, in which (1) the oligomer of the present invention, (2) trimethoxymethylmelamine and (3) urea are in the range of (1):(2)+(3)=80:20 to 90:10 and (2):(3)=50:50 to 25:75.

EXAMPLE 17

A blend-spun shirting of polyester/cotton (65/35) was treated in the same way as in Example 16 with a treating liquid of the following composition and then subjected to oxidation treatment, rinsed with water and dried.

| Treating liquid: | |
|---|---|
| Phosphonium oligomer (80%) (adjusted to a pH of 5.2 with a 20% aqueous solution of sodium hydroxide) | 66 parts |
| Urea | 6 parts |
| Sumitex Resin M-3 | 4 parts |
| Polyethylene glycol (MW = 600) | 2 parts |
| Eleganol SRT-1 | 2 parts |
| DIC Silicone Softener TS | 0.5 part |
| Liponox NA | 0.1 part |
| Water | balance |
| Total | 120 parts |

The percent phosphorus content, flame retardancy and hand of the thus treated cloth were evaluated and the results in Table 7 were obtained.

Table 7

| Experiment No. | Present invention | | | Comparative example | | | Untreated |
|---|---|---|---|---|---|---|---|
| | 23 | 24 | 25 | 26 | 27 | 28 | |
| Phosphonium oligomer | | | | | | | |
| Example | 1 | 4 | 8 | | | | |
| Comparative Example | | | | 1 | 2 | 3 | |
| Flame retardancy (cm.)* | | | | | | | |
| Before washing | 9.6 | 9.5 | 9.5 | 9.6 | BEL | BEL | BEL |
| After 50 washings** | 10.1 | 9.3 | 10.8 | BEL | BEL | BEL | BEL |
| Hand Handl-o-meter (g.) | 67 | 70 | 71 | 67 | 65 | 60 | 30 |
| % P content | | | | | | | |
| Before washing | 5.1 | 5.1 | 5.1 | 3.9 | 2.8 | 0.26 | |
| After 50 washings** | 4.0 | 4.3 | 3.9 | 2.7 | 1.9 | 0.13 | |
| % retension | 78 | 84 | 76 | 69 | 68 | 50 | |

*DOCFF3-71
**AATCC 124 III B Method

The phosphonium oligomer for which dicyandiamide was used as catalyst showed particularly excellent durability but it had a tendency to give somewhat stiff hand.

EXAMPLE 18

A blend-spun shirting (45's×45's/86×82) of Dacron T 900 F (E. I. DU PONT; flame retardancy-modified polyester fiber)/cotton (65/35) was padded with a treating liquid of the following composition. After the cloth was squeezed to a wet pickup of 82%, it was dried at 80° C. for 7 minutes and heat-treated at 160° C. for 3 minutes. In the same way as in Example 15, the cloth was subjected to oxidation treatment, rinsed with water and dried.

| Treating liquid: | |
|---|---|
| Phosphonium oligomer in Example 4 (80%) (adjusted to a pH of 5.2) | 46 parts |
| Urea | 4.2 parts |
| Sumitex Resin M-3 | 2.8 parts |
| Polyethylene glycol (MW = 600) | 2.8 parts |
| Eleganol SRT-1 | 2.1 parts |
| DIC Silicone Softener-TS | 0.4 part |
| Liponox NA | 0.1 part |
| Water | balance |
| Total | 100 parts |

The percent phosphorus content, flame retardancy and stiffness of the thus-treated cloth were evaluated and the results in Table 8 were obtained.

Table 8

| Experiment No. | | 29 | Untreated |
|---|---|---|---|
| Flame retardancy (cm)* | Before washing | 10.2 | BEL |
| | After 50 washings** | 12.1 | " |
| Phosphorus content (%) | Before washing | 3.50 | — |
| | After 50 washings** | 2.85 | — |
| | % retension | 81 | — |
| Hand | Stiffness (mm) | 75 | 63 |
| | Increase in stiffness (%) | 19 | |

*DOCFF 3-71
**AATCC 124 III-B method

By treating the blend-spun cloth of flame retardancy-modified polyester/cotton, a good hand and durable flame retardancy were obtained.

EXAMPLE 19

A blend-spun lawn of polyester/cotton (45/55) was padded with a treating liquid of the following composition. After the cloth was squeezed to a wet pickup of 100%, it was dried at 80° C. for 10 minutes and heat-treated at 160° C. for 3 minutes. In the same way as in Example 15, the cloth was then subjected to oxidation treatment, rinsed with water and dried.

| Treating liquid: | |
|---|---|
| Phosphonium oligomer in Example 3 (80%) (adjusted to a pH of 5.2) | 39.6 parts |
| Fyrol 76 (Stauffer Chemical; flame retardant) | 16 parts |
| N-methylolacrylamide (60%) | 4 parts |
| Potassium persulfate | 0.4 part |
| Sumitex Resin M-3 | 6.2 parts |
| Polyethylene glycol (MW = 600) | 4 parts |
| Eleganol SRT-1 | 3 parts |
| DIC Silicone Softener | 0.5 part |
| Liponox NA | 0.1 part |
| Water | balance |
| Total | 120 parts |

The percent phosphorus content, flame retardancy and hand of the treated cloth are shown in Table 9.

Table 9

| Experiment No. | | 30 | Untreated |
|---|---|---|---|
| Flame retardancy (cm) | Before washing | 12.1 | BEL |
| | After 10 washings** | 15.6 | " |
| Phosphorus content (%) | Before washing | 4.02 | |
| | After 10 washings** | 3.31 | |
| | % retension | 82 | |
| Hand | Stiffness (mm) | 56 | 37 |
| | Increase in stiffness (%) | 51 | |

*DOCFF 3-71
**AATCC 124 III-B Method

By using the phosphonium oligomer and radical polymerization-type flame retardant in combination, it was also possible to further improve the hand and flame retardancy.

EXAMPLE 20

500 g. of 80% THPA was adjusted to a pH of 1.0 with hydrogen chloride aqueous solution. Then, this mixture was condensed in the same way as Example 1. After the contents of the flask were cooled, an amount of water was added to the nonflowable resinuous substance thus obtained to make it up to a 80% aqueous solution. A blend spun shirting of polyester/cotton (50/50) was treated in the same way as Experiment No. 21 in Example 16. This fabric provided excellent flame retardancy after 50 times washing.

EXAMPLE 21

500 g. of 80% tetrakis(hydroxymethyl)phosphonium sulfate and 25 g. of sodium chloride were condensed in the same way as Example 1. After the contents of the flask were cooled, an amount of water was added to the nonflowable resinous substance thus obtained to make it up to an 80% aqueous solution. A blend spun shirting of polyester/cotton (50/50) was treated in the same way as Experiment No. 21 in Example 16. This fabric provided excellent flame retardancy after 50 times washing.

What we claim is:

1. A process for producing a water-soluble phosphorus-containing condensation product having a molar ratio P—CH$_2$—P linkage/P—CH$_2$OCH$_2$—P linkage of 0.8–4.0, which comprises heating a tetrakis(hydroxymethyl)phosphonium compound under acid conditions at a temperature exceeding 150° C. and a pressure below 100 mm Hg to condense said phosphonium compound by dehydration and deformaldehydation reaction.

2. The process as claimed in claim 1 wherein the molar ratio P—CH$_2$—P linkage/P—CH$_2$OCH$_2$—P linkage of said water-soluble phosphorus-containing condensation product is 1.0–2.0.

3. The process as claimed in claim 1 wherein the heating temperature is a temperature between 151° and 180° C. and the pressure is between 30 and 70 mm Hg.

4. The process as claimed in claim 1 wherein the tetrakis(hydroxymethyl)phosphonium compound is tetrakis)hydroxymethyl)phosphonium chloride or tetrakis(hydroxymethyl)phosphonium acetate.

5. The process as claimed in claim 1 wherein the said acid conditions are below pH 4.

6. A process for producing a water-soluble phosphorus-containing condensation product having a molar ratio P—CH$_2$—P linkage/P—CH$_2$OCH$_2$—P linkage of 0.8–4.0, which comprises heating a tetrakis(hydroxymethyl)phosphonium compound under acid conditions in the presence of, as catalyst, 0.001–0.2 mol of an amino group-containing compound per mol of said phosphonium compound, at a temperature exceeding 120° C. and a pressure below 100 mm Hg to condense said phosphonium compound by dehydration and deformaldehydation reaction.

7. The process as claimed in claim 6 wherein 0.001–0.02 mol of the amino-group-containing compound is used per mol of the tetrakis(hydroxymethyl)phosphonium compound.

8. The process as claimed in claim 6 wherein the amino group-containing compound is dicyandiamide, guanidine, urea, ethylene urea or melamine.

9. The process as claimed in claim 7 wherein the amino group-containing compound is dicyandiamide.

10. The process as claimed in claim 6 wherein the molar ratio P—CH$_2$—P linkage/P—CH$_2$OCH$_2$—P linkage of said water-soluble phosphorus-containing condensation product is 1.0–2.0.

11. The process as claimed in claim 6 wherein the heating temperature is a temperature between 135° and 160° C., and the pressure is between 30 and 70 mm Hg.

12. The process as claimed in claim 6 wherein the tetrakis(hydroxymethyl)phosphonium compound is tetrakis(hydroxymethyl)phosphonium chloride or tetrakis(hydroxymethyl)phosphonium acetate.

13. The process as claimed in claim 6 wherein the said acid conditions are below pH 4.

* * * * *